United States Patent [19]

Shimizu et al.

[11] Patent Number: 5,227,550
[45] Date of Patent: Jul. 13, 1993

[54] METHOD FOR PREPARATION OF METHYL CHLORIDE

[75] Inventors: Takaaki Shimizu; Taishi Kobayashi; Hironori Iwasaki, all of Niigata, Japan

[73] Assignee: Shin-Etsu Chemical Co., Ltd., Tokyo, Japan

[21] Appl. No.: 884,272

[22] Filed: May 13, 1992

Related U.S. Application Data

[63] Continuation of Ser. No. 633,006, Dec. 24, 1990, abandoned.

[30] Foreign Application Priority Data

Dec. 26, 1989 [JP] Japan ................................. 1-339095

[51] Int. Cl.$^5$ .............................................. C07C 17/16
[52] U.S. Cl. ...................................... 570/261; 570/258
[58] Field of Search .............................. 570/261, 258

[56] References Cited

U.S. PATENT DOCUMENTS

| | | | |
|---|---|---|---|
| 2,172,568 | 9/1939 | Rothweiler | 570/261 |
| 2,847,484 | 8/1958 | Kolker | 570/258 |
| 4,423,024 | 12/1983 | Wolford | 423/437 |

*Primary Examiner*—Marianne M. Cintins
*Assistant Examiner*—Kimberly J. Kestler
*Attorney, Agent, or Firm*—Wenderoth, Lind & Ponack

[57] ABSTRACT

Carbon tetrachloride, which is a material of low value and may be banned due to the problem of the destructiveness against the stratospheric ozone layer, can be efficiently utilized in the preparation of more useful methyl chloride by a catalytic vapor-phase reaction in a vapor mixture of carbon tetrachloride, methyl alcohol and water. The solid catalyst with which the vapor mixture is contacted at 150° to 250° C. is, for example, a zinc chloride catalyst supported on an active carbon carrier. The conversion of carbon tetrachloride is almost 100% when the contacting time is 10 to 20 seconds.

6 Claims, No Drawings

METHOD FOR PREPARATION OF METHYL CHLORIDE

This application is a continuation of now abandoned application, Ser. No. 07/633,006, filed Dec. 24, 1990, abandoned.

BACKGROUND OF THE INVENTION

The present invention relates to a method for the utilization of carbon tetrachloride. More particularly, the invention relates to a method for the utilization of carbon tetrachloride, which may cause a problem of environmental pollution, in the preparation of methyl chloride as a useful chemical compound.

As is well known, as one of the serious issues in recent years relative to environmental pollution, carbon tetrachloride is, besides specific fluorocarbon compounds and the like chemical compounds, notoriously destructive against the stratospheric ozone layer.

According to an established international agreement, certain fluorocarbons are to be banned in the near future or even within this century, and intensive investigations are now under way in various industrial fields for replacing fluorocarbons with harmless substitutes to comply with this requirement. It should be noted here, however, that several chlorine-containing organic comounds are comparable with or even worse than the fluorocarbon compounds in respect of the destructiveness against the stratospheric ozone layer. Carbon tetrachloride is one of such chlorine-containing compounds. For example, the ozone-destruction index of carbon tetrachloride is estimated to be 1.0 to 1.2 assuming that the values for trichlorofluoromethane and dichlorodifluoromethane are each 1.0. In addition, carbon tetrachloride is suspected to be responsible for the tendency toward global warming by the greenhouse effect for which carbon dioxide is assumed to have the principal responsibility. Accordingly, it is an inevitable trend that carbon tetrachloride is also entirely placed under a ban sooner or later.

As is known, carbon tetrachloride is produced in two industrial processes. One of the processes is the reaction of carbon disulfide with chlorine according to the reaction equation $$CS_2 + 3Cl_2 \rightarrow CCl_4 + S_2Cl_2.$$

This reaction is a single-step reaction producing only carbon tetrachloride and sulfur chloride. Since sulfur chloride can be produced also in a different process, there will hardly be caused any problem in the chemical industry even when the process utilizing the above reaction is entirely discontinued.

Alternatively, carbon tetrachloride is being manufactured by the direct chlorination of methane with chlorine. The reaction here proceeds as a successive chlorination of methane concurrently producing methyl chloride, methylene chloride, chloroform and carbon tetrachloride. The reaction mixture after the reaction is usually a mixture of these four chlorides of methane together with unreacted methane. Each of the intermediate chlorination products of methane, i.e. the chloromethanes other than carbon tetrachloride, is an industrially important compound and is consumed in a large quantity. In other words, carbon tetrachloride is produced as an undesirable by-product in the production of these useful intermediate chlorination products of methane. Accordingly, it is a due expectation that there will be caused a great problem in the chemical industry when the above described process for the direct chlorination of methane is entirely discontinued since no other industrially feasible processes comparable to the direct chlorination of methane are known for the production of the intermediate chlorination products of methane. Accordingly, production of carbon tetrachloride as a by-product in this process is, so to say, a necessary evil.

It is therefore an important technical problem to develop an efficient industrial method for the disposal of carbon tetrachloride without causing any problems of environmental pollution, or rather for the conversion of carbon tetrachloride into useful and harmless compounds. Several proposals and attempts have been made hitherto in this purpose. They are, for example, as follows.

Firstly, carbon tetrachloride can be reduced with hydrogen into lower chlorination products of methane such as chloroform and methylene chloride in the presence of a Raney nickel catalyst. This method, however, has serious problems in respect of the low reaction velocity, insufficient life of the catalyst, formation of a large amount of by-products such as 1,2-dichloroethane and the like, so that this method is still at the stage of laboratory investigations.

Secondly, carbon tetrachloride is subjected to a combustion reaction with a fuel gas such as methane, LPG and the like in the presence of air to be converted into carbon dioxide and hydrogen chloride. This process is of course disadvantageous because, even by setting aside the problem of large consumption of the fuel gas, the combustion temperature is so high as to necessitate use of a highly refractory combustion furnace having high resistance against corrosive hydrogen chloride. Moreover, the products of the process are each a material of low added value capable of being produced at low costs in other large-scale industrial processes.

Apart from the above described direct chlorination of methane, methyl chloride can be industrially produced by the reaction of methyl alcohol and hydrogen chloride. This process is usually performed in the gaseous phase in the presence of a solid catalyst because the velocity of the reaction is low in the liquid phase and hardly achieves sufficient utilization of the starting materials. The above mentioned solid catalyst for the vapor-phase reaction of methyl alcohol and hydrogen chloride usually contains a catalytically active metallic element including the elements of the Group IB, e.g., copper, elements of the Group IIA, e.g., magnesium, calcium and barium, elements of the Group IIB, e.g., zinc, cadmium and mercury, elements of the Group VIB, e.g., chromium and molybdenum, elements of the Group VIIB, e.g., manganese, and elements of the Group VIII, e.g., iron, cobalt and nickel, of the Periodic Table in the form of an oxide or halide supported on a solid carrier such as alumina, pumice, kaolin, zeolite, active carbon and the like.

An idea would be to develop a process in which carbon tetrachloride is utilized in an industrial process for the preparation of methyl chloride, possibly, by the reaction with methyl alcohol according to the reaction equation of:

$$4CH_3OH + CCl_4 \rightarrow 4CH_3Cl + 2H_2O + CO_2. \tag{1}$$

This reaction is a sequential combination of the two elementary reactions expressed by the reaction equations of:

$$CCl_4 + 2H_2O \rightarrow CO_2 + 4HCl \qquad (2)$$

and $$4CH_3OH + 4HCl \rightarrow 4CH_3Cl + 4H_2O. \qquad (3)$$

Namely, carbon tetrachloride is first hydrolyzed in the reaction (2) by reacting with atmospheric moisture and the hydrogen chloride produced by the reaction (2) pertains to the esterification reaction of methyl alcohol according to the equation (3).

In so far as the matter concerns the esterification reaction of methyl alcohol only, no particular difference can be seen in the catalytic performance of the above described various catalysts and satisfactory results can be obtained with any one of those catalysts. In the reaction of methyl alcohol with carbon tetrachloride, in which the esterification reaction must be preceded by the hydrolysis reaction of carbon tetrachloride, however, no quite satisfactory results have yet been reported for the conversion of methyl alcohol into methyl chloride at an industrially feasible velocity in a high yield. This is because the rate-determining reaction in the sequence of the reactions (2) and (3) is the step of the reaction (2) which is of a quite different nature from the reaction (3).

Japanese Patent Kokai 56-167628 and 57-165330 disclose a process for the reaction of methyl alcohol in the vapor phase with hydrogen chloride gas containing methylene chloride, chloroform and carbon tetrachloride in the presence of a zinc chloride catalyst supported on an alumina carrier. This process, however, is for the preparation of methyl chloride from methyl alcohol by the reaction with hydrogen chloride gas, which is a by-product in the direct chlorination of methane and necessarily contains the chloromethanes when no isolation step is undertaken to remove the chloromethanes. In this process, accordingly, it is assumed that the chloromethane compounds, i.e. methylene chloride, chloroform and carbon tetrachloride, are contained intact in the reaction product.

The teaching in the above mentioned Japanese Patent Kokai 56-167628 is given with an object to prevent deactivation of the zinc chloride catalyst on alumina by the deposition of carbon produced by the decomposition of chloroform and carbon tetrachloride while Japanese Patent Kokai 57-165330 teaches a method in which decomposition of methylene chloride, chloroform and carbon tetrachloride can be completely prevented, according to the examples, by using a catalyst of zinc chloride on an alumina carrier.

SUMMARY OF THE INVENTION

The present invention accordingly has an object to provide a method for the utilization of carbon tetrachloride of relatively low usefulness or, rather, as a nuisance in the production of an industrially more useful product such as methyl chloride, by the reaction with methyl alcohol in a high yield at an industrially feasible velocity.

Thus, the method of the invention for the utilization of carbon tetrachloride in the preparation of methyl chloride comprises: contacting a vapor mixture of carbon tetrachloride and methyl alcohol in a molar ratio of 1.01 to 2.0 moles of carbon tetrachloride per 4 moles of methyl alcohol under a pressure up to 10 kg/cm²G at a temperature in the range from 150° to 250° C. with a solid catalyst comprising, as an active ingredient, a halide or oxide of an element selected from the group of the elements belonging to the Groups IB, IIA, IIB, VIB, VIIB and VIII of the Periodic Table, supported on active carbon as a carrier. The contacting time of the vapor mixture with the solid catalyst is usually in the range from 1 to 60 seconds.

It is sometimes advantageous that the vapor mixture further contains hydrogen chloride or water.

DETAILED DESCRIPTION OF THE PREFERRED EMBODIMENTS

The reaction of the above described process for obtaining methyl chloride from carbon tetrachloride by the reaction with methyl alcohol is expressed by the overall reaction equation $$4CH_3OH + CCl_4 \rightarrow 4CH_3Cl + 2H_2O + CO_2. \qquad (1)$$

This overall reaction equation is a combination of two elementary reaction equations including $$CCl_4 + 2H_2O \rightarrow CO_2 + 4HCl \qquad (2)$$

for the hydrolysis reaction of carbon tetrachloride and $$4CH_3OH + 4HCl \rightarrow 4CH_3Cl + 4H_2O \qquad (3)$$

for the esterification reaction of methyl alcohol.

The catalytically active ingredient in the solid catalyst used in the inventive method is a halide or oxide of an element selected from the group consisting of the elements belonging to the Group IB, e.g., copper, Group IIA, e.g., magnesium, calcium and barium, Group IIB, e.g., zinc, cadmium and mercury, Group VIB, e.g., chromium and molybdenum, Group VIIB, e.g., manganese, and Group VIII, e.g., iron, cobalt and nickel, of the Periodic Table. These catalytically active ingredients are supported on active carbon as the solid carrier. Among the above named catalytically active ingredients, halides and oxides of the Group VIII metals and halides of the Group IIB metals are preferred in respect of the reaction velocity. Zinc chloride is the most preferable.

The solid carrier in the preparation of the catalyst used in the inventive method is active carbon by virtue of which the reaction velocity of the above mentioned first elementary reaction (2), which is rate-determining of the overall reaction expressed by the equation (1), is greatly increased to give methyl chloride in a high yield at a large reaction velocity. This advantageous effect is due at least partly to the relatively large specific surface area of active carbon amounting to 700 to 1500 m²/g, as compared with alumina having a specific surface area of 150 to 350 m²/g, silica having a specific surface area of 200 to 600 m²/g, activated clay having a specific surface area of 100 to 250 m²/g and synthetic zeolite having a specific surface area of 400 to 750 m²/g.

The reaction of the inventive method is performed at a temperature in the range from 150° to 250° C. When the reaction temperature is too low, the velocity of the reaction is disadvantageously low. When the temperature is too high, on the other hand, the advantages obtained by the increase in the reaction velocity are negated due to the serious corrosion of the reactor, necessitating use of highly corrosion-resistant but very expensive materials. The pressure of the gaseous reaction mixture is preferably in the range from normal pressure to 10 kg/cm$^2$G. Further increase in the reaction pressure gives an advantage that the capacity of the reactor can be decreased to a very small one, but a problem is caused thereby in the selection of the material of the reactor which must have a sufficiently high mechanical strength even under the corrosive conditions. When the above specified temperature and pressure are undertaken in a continuous process of passing a gaseous mixture of methyl alcohol and carbon tetrachloride through a catalyst bed, conversion of carbon tetrachloride can be as high as 95% or more by a contacting time of 1 to 60 seconds or, in most cases, 10 to 20 seconds to react with methyl alcohol. The selectivity of the catalytic reaction is very high and almost all of the consumed carbon tetrachloride can be converted into methyl chloride with a very small amount of by-products. It is preferable that the proportion of the carbon tetrachloride relative to methyl alcohol in the gaseous mixture introduced into the reactor is somewhat in excess over the stoichiometric proportion or, in other words, 4 moles of methyl alcohol are admixed with carbon tetrachloride in an amount somewhat larger than 1 mole or, preferably, in the range from 1.01 to 2.0 moles.

It is sometimes advantageous that the vapor mixture of carbon tetrachloride and methyl alcohol is further admixed with hydrogen chloride. The amount of hydrogen chloride to be added to the gaseous reactant mixture should preferably be such that the molar ratio of (4CCl$_4$+HCl)/CH$_3$OH is in the range from 1.01 to 1.30. When this molar ratio is smaller than 1.01, the amount of unreacted methyl alcohol would be increased along with an increase in the amount of dimethyl ether as a by-product formed by the dehydration reaction of methyl alcohol. Though not critical, an increase in the molar ratio over the above mentioned upper limit may decrease the efficiency of chlorine utilization into methyl chloride along with an increase in the amount of unreacted hydrogen chloride.

When the reaction system is designed as an industrial process, it is advantageous that the gaseous reactant mixture is admixed with a substantial amount of hydrogen chloride. It is economically advantageous in the chlorination process of methane or methyl chloride with chlorine in which carbon tetrachloride is produced as a by-product that a reactor is installed for the conversion of hydrogen chloride into methyl chloride by the reaction with methyl alcohol. When the process of the inventive method is performed in the same reactor as above, the overall process for the production of chloromethanes can be freed from the problem due to carbon tetrachloride formed as an undesirable by-product. In most cases of the chlorination process of methane or methyl chloride, the hydrogen chloride formed as a by-product is used in the form of aqueous hydrochloric acid by being absorbed in water. In the process of the inventive method, there would be caused no adverse influences by the presence of water in the gaseous reactant mixture mainly composed of the vapors of carbon tetrachloride, methyl alcohol and hydrogen chloride or, rather, an advantage is obtained by the presence of water that the hydrolysis reaction of carbon tetrachloride by the reaction (2) is promoted.

As is shown by the overall reaction equation (1) for the process of the inventive method, carbon dioxide is produced as a by-product in an amount of one fourth of methyl chloride by moles. The carbon dioxide can be readily removed from the gaseous mixture of the product by any conventional method such as absorption in sodium hydroxide, alkali carbonate, ethanol amine and the like.

In the following, examples are given to illustrate the method of the invention in more detail but not to limit the scope of the invention in any way. As is understood from these examples, the present invention provides a very efficient method for the conversion of carbon tetrachloride of less value into more useful methyl chloride by the catalytic reaction carried out at a relatively low temperature of 150° to 250° C. in a very short contacting time of 10 to 20 seconds, and the conversion of carbon tetrachloride is almost 100%.

EXAMPLE 1

A glass-made tubular reactor having an inner diameter of 45 mm was filled to form a catalyst bed of 450 mm length with a solid catalyst supporting 30% by weight of zinc chloride on pellets of active carbon having a diameter of 4 mm and a length of 6 mm, of which the specific surface area was 1500 m$^2$/g, and the catalyst bed was kept at 200° C. A gaseous mixture of carbon tetrachloride, methyl alcohol and hydrogen chloride was continuously introduced into the reactor over 100 hours under normal pressure. The hourly feed rates were 56.2 g (0.365 mole) for carbon tetrachloride, 130.9 g (4.091 moles) for methyl alcohol and 111.0 g (3.042 moles) for hydrogen chloride.

The gaseous mixture coming out of the reactor was cooled and partly condensed in a water-cooled condenser and the uncondensed gas from the condenser was bubbled into an ice water bath so as to have the water-soluble constituents absorbed therein. The amounts of the condensate in the condenser and the increment in the weight of the ice water bath were recorded. The volume of the gas coming from the ice water bath was measured in a gasometer. The rate of gas introduction into the gasometer was constant over the reaction time of 100 hours.

Each of the above obtained condensate in the condenser, water of the ice water bath and the gas entering the gasometer was analyzed for the contents of the following constituents.

Condensate: hydrogen chloride, methyl alcohol and chloromethanes

Ice water bath: hydrogen chloride, methyl alcohol and chloromethanes

Gasometer gas: methyl alcohol, chloromethanes, carbon monoxide, carbon dioxide and dimethyl ether The results of the analyses are summarized below as an average of the analytical values for the reaction time for each constituent analyzed in one or more of the three samples.

| | |
|---|---|
| Methyl chloride | 4.080 moles/hour |
| Carbon dioxide | 0.355 mole/hour |
| Methyl alcohol | 0.011 mole/hour |
| Hydrogen chloride | 0.382 mole/hour |
| Water | 4.080 moles/hour |
| Carbon tetrachloride | 0.010 mole/hour |
| Dimethyl ether | trace |
| Methylene chloride | not detected |
| Chloroform | not detected |
| Carbon monoxide | not detected |

The conversions of carbon tetrachloride and methyl alcohol were 97.2% and 99.7%, respectively, as calculated from the above obtained analytical results.

EXAMPLE 2

The reaction procedure was substantially the same as in Example 1 except that the hourly feed rates of the carbon tetrachloride and methyl alcohol were 173.3 g (1.125 moles) for carbon tetrachloride and 130.9 g (4.091 moles) for methyl alcohol and hydrogen chloride was omitted in the gaseous feed. The reaction proceeded as smoothly as in Example 1 over the reaction time of 100 hours. The results of the analyses are summarized below.

| | |
|---|---|
| Methyl chloride | 4.058 moles/hour |
| Carbon dioxide | 1.091 moles/hour |
| Methyl alcohol | 0.033 mole/hour |
| Hydrogen chloride | 0.306 mole/hour |
| Water | 4.058 moles/hour |
| Carbon tetrachloride | 0.034 mole/hour |
| Dimethyl ether | trace |
| Methylene chloride | not detected |
| Chloroform | not detected |
| Carbon monoxide | not detected |

The conversions of carbon tetrachloride and methyl alcohol were 97.0% and 99.2%, respectively, as calculated from the above obtained analytical results.

COMPARATIVE EXAMPLE

The experimental conditions were substantially the same as in Example 1 described above except that beads of alumina of 4 to 5 mm diameter having a specific surface area of 150 m$^2$/g were used as the carrier of the zinc chloride catalyst in place of the active carbon pellets. The volume of the gas entering the gasometer began to decrease after 50 hours of running and the reaction must be discontinued after 60 hours from the start due to the extreme decrease in the volume of the gas entering the gasometer. The results of the analyses averaged for 60 hours of the reaction time were as follows.

| | |
|---|---|
| Methyl chloride | 2.586 moles/hour |
| Carbon dioxide | 0.274 mole/hour |
| Methyl alcohol | 1.501 moles/hour |
| Dimethyl ether | 0.002 mole/hour |
| Hydrogen chloride | 1.560 moles/hour |
| Water | 2.586 moles/hour |
| Carbon tetrachloride | 0.080 mole/hour |
| Methylene chloride | not detected |
| Chloroform | not detected |
| Carbon monoxide | not detected |

The conversions of carbon tetrachloride and methyl alcohol were 75.0% and 63.3%, respectively, as calculated from the above obtained analytical results.

What is claimed is:

1. A method for preparation of methyl chloride which comprises: contacting a vapor mixture containing carbon tetrachloride and methyl alcohol and water in a molar ratio of 1.01 to 2.0 moles of carbon tetrachloride per 4 moles of methyl alcohol under a pressure up to 10 kg/cm$^2$G at a temperature in the range from 150° to 250° C. with a solid catalyst comprising, as an active ingredient, a halide or oxide of an element selected from the group of the elements belonging to the Groups IB, IIA, IIB, VIB, VIIB and VIII of the Periodic Table, supported on active carbon as a carrier.

2. The method as claimed in claim 1 in which the active ingredient supported on the carrier is zinc chloride.

3. The method as claimed in claim 1 in which the vapor mixture further contains hydrogen chloride.

4. The method as claimed in claim 3 in which the amount of the hydrogen chloride contained in the vapor mixture satisfies the relationship that the molar ratio of (4CCl$_4$+HCl)/CH$_3$OH is in the range from 1.01 to 1.30.

5. The method as claimed in claim 1 in which the vapor mixture is contacted with the solid catalyst for a length of time in the range from 1 to 60 seconds.

6. A method for preparation of methyl chloride which comprises:
   providing a vapor mixture containing carbon tetrachloride, methyl alcohol and water in a molar ratio of 1.01 to 2.0 moles of carbon tetrachloride per 4 moles of methyl alcohol,
   introducing said mixture into a reactor containing a solid catalyst comprising, as an active ingredient, a halide or oxide of an element selected from the group of the elements belonging to the Groups IB, IIA, IIB, VIB, VIIB and VIII of the Periodic Table, supported on active carbon as a carrier, and
   contacting said mixture with said catalyst in said reactor under a pressure up to 10 kg/cm$^2$G at a temperature in the range of from 150° to 250° C.

* * * * *